United States Patent [19]

Miya et al.

[11] 4,214,101

[45] Jul. 22, 1980

[54] PROCESS FOR PREPARING ETHER CARBOXYLATES

[75] Inventors: Bunji Miya; Akio Kimura, both of Wakayama, Japan

[73] Assignee: Kao Soap Co., Ltd., Tokyo, Japan

[21] Appl. No.: 896,088

[22] Filed: Apr. 13, 1978

[30] Foreign Application Priority Data

May 16, 1977 [JP] Japan .................................. 52-56205

[51] Int. Cl.$^2$ ...................... C07C 51/24; C07C 59/00
[52] U.S. Cl. .................................... 562/421; 562/489; 562/496; 562/537; 562/538; 562/587; 260/406
[58] Field of Search ............... 260/406, 413 R, 413 J, 260/413 Q, 413 M; 562/421, 489, 496, 470, 537, 538, 582, 587

[56] References Cited

U.S. PATENT DOCUMENTS

| | | | |
|---|---|---|---|
| 2,653,972 | 9/1953 | Ash | 562/537 |
| 3,342,858 | 9/1967 | Fuhrmann | 562/537 |
| 3,595,909 | 7/1971 | Sheldon | 562/538 |
| 3,890,381 | 6/1975 | Kiyoura | 562/537 |

FOREIGN PATENT DOCUMENTS

880524 10/1961 United Kingdom ..................... 562/587

*Primary Examiner*—John F. Niebling
*Attorney, Agent, or Firm*—Blanchard, Flynn, Thiel, Boutell & Tanis

[57] ABSTRACT

A process for preparing ether carboxylates which comprises contacting an ethoxylated alcohol or alkylphenol or an ethylene oxide/propylene oxide block copolymer, with oxygen, in the presence of a palladium catalyst, at a pH of from 8 to 13 and at a temperature of 50° to 95° C.

8 Claims, No Drawings

PROCESS FOR PREPARING ETHER CARBOXYLATES

BACKGROUND OF THE INVENTION

1. Field of the Invention

The present invention relates to a process for preparing ether carboxylates. More particularly, the invention relates to a process comprising oxidizing an ethoxylated primary alcohol or alkylphenol having a terminal hydroxy group or a polyoxyethylene/polyoxypropylene block copolymer, with oxygen, in the presence of water and a palladium catalyst, to convert the terminal —CH$_2$OH group to a carboxyl group and simultaneously neutralizing the thus-formed carboxyl group with an alkali whereby to form an alkali salt of the carboxylic acid.

2. Description of the Prior Art

A process for oxidizing primary alcohols, in the presence of a noble metal catalyst, with an oxygen-containing gas is known, and this process is outlined on page 303, volume 2 of "Newer Methods of Preparative Organic Chemistry" (Academic Press, New York, 1963). In the process described in this literature reference, an expensive platinum catalyst is exclusively used in a large amount, and therefore, this process is not suitable for the oxidation of nonionic surface active agents which is an intended use of the present invention. Japanese Patent Application Laid-Open Specification No. 34122/73 discloses a process comprising oxidizing and neutralizing one or two terminal primary hydroxy groups of polyethylene glycol to form a mono- or dicarboxylic acid salt. Pt or Pd is used as a catalyst in this process and the amount of the catalyst is very large, such as 30 to 138% based on the polyethylene glycol. Further, a long time is required and the concentration of polyethylene glycol is lower than 10% as is seen in the Examples of this publication. Even under these preferred conditions, the conversion is not very high. Moreover, as will be apparent from Examples 3, 7 and 8 of this publication, the conversion is drastically lowered as the polyoxyethylene chain becomes longer. For example, when the reaction is carried out at 35° C. in the presence of a 5%-Pt/carbon catalyst, 2% of the mono-salt and 98% of the di-salt are obtained from diethylene glycol under conditions wherein the catalyst amount is 30% and the reaction time is 7 hours, but when triethylene glycol is used, 71.8% of the mono-salt and 20.5% of the di-salt are obtained by conducting the reaction for 9 hours. Moreover, in the case of polyethylene glycol 300, only 3.5% of the mono-salt and 7.5% of the di-salt are obtained by conducting the reaction for 5 hours. From the fact that when a 5%-Pd/carbon catalyst is used in an amount of 114% based on the diethylene glycol and the reaction is carried out for 7 hours, the product consists of 87% of the mono-salt and 12% of the di-salt (see Example 5), it is apparent that this 5-% Pd/carbon catalyst is not superior to a 5-% Pt/carbon catalyst. Accordingly, is cannot be expected from the teachings of this reference that a palladium catalyst can be used advantageously in industry for the oxidation of compounds having a polyoxyethylene chain in the molecule.

SUMMARY OF THE INVENTION

To our surprise, we found that oxidation of an ethoxylated primary aliphatic alcohol or alkylphenol having a terminal hydroxy group or an ethylene oxide/propylene oxide block copolymer can be completed in a short time in the presence of a small amount of palladium catalyst, using an aqueous solution or dispersion of the starting material of a relatively high concentration. On the basis of this finding, we have now completed the present invention.

The starting material used in the invention comprises compounds having the formula RO(CH$_2$CH$_2$O)$_n$H, wherein R is alkyl having 8 to 22 carbon atoms, octylphenyl, nonylphenyl or dodecylphenyl, and n is an integer of from 1 to 100. When R is alkyl (C$_8$ to C$_{22}$), the compounds are generally referred to as ethoxylated aliphatic alcohols. When R is octylphenyl, nonylphenyl and dodecylphenyl, the compounds are referred to as ethoxylated alkylphenols. Both of these materials are known nonionic surfactants. Another useful starting material has the formula HO(CH$_2$CH$_2$O)$_a$(C$_3$H$_6$O)$_b$(CH$_2$CH$_2$O)$_c$H, wherein "a", "b" and "c" are such that the average molecular weight of the material is from 1000 to 12000 and the total amount of CH$_2$CH$_2$O units is from 10 to 80% of the total weight of the material. These materials are commonly referred to as polyoxypropylenepolyoxyethylene nonionic surfactants. For convenience in description, these starting materials are sometimes hereinafter referred to as ether-type nonionic surface active agents.

According to the present invention, the starting material need not be used in the form of a true aqueous solution. In other words, an aqueous solution or a aqueous dispersion comprising a dispersed phase of the starting material and an aqueous phase can be employed in the reaction. Further, because the concentraion of the starting material based on the entire reaction mixture can be increased so as to be above 10 wt. %, the oxidation reaction can be carried out advantageously on an industrial basis. However, if the concentration of the starting material agent is too high, at a certain level of conversion, the viscosity is abruptly increased whereby to render insufficient the contact of the reaction mixture with the oxygen, and it becomes impossible to further conduct the reaction. Accordingly, the concentration of the starting material should be maintained below a certain level. The viscosity of the reaction mixture, however, in this case also, attains a maximum when the conversion reaches a certain level, but if the conversion rises farther, the viscosity of the reaction mixture is reduced again and the reaction can further progress. Because the optimum concentration of the starting material in the starting reaction mixture varies, depending on the specific type of the starting material used and the length of the ethylene oxide chain therein, the optimum concentration should be determined from routine experiments conducted in advance. In general, good results are obtained when the concentration of the starting material in the starting reaction mixture is from about 10 to about 40% by weight.

According to the description given on page 303, volume 2 of "Newer Methods of Preparative Organic Chemistry" (Academic Press, New York, 1963), when the concentration of the reactant exceeds 10%, the reaction rate is reduced and the yield is lowered, and therefore, the suitable concentration of the reactant is 2 to 7%. Further, it is taught that when a water-soluble alcohol is used, it should be dissolved in water and that when a water-soluble alcohol is used, it should be dissolved in an organic solvent. The use of an organic solvent is not only disadvantageous economically, but also the coexistence of an organic substance and oxygen in the presence of a noble metal catalyst involves a risk of explosion and is very dangerous. Accordingly, in order to perform oxidation of primary alcohols with safety on an industrial scale, it is necessary to use aqueous solutions of these alcohols. The above reference also teaches that the liquid reaction mixture should be completely homogeneous and if even a very small amount of a second phase, for example, of oil drops, is present in the aqueous phase, coagulation of the catalyst takes place and the reaction is immediately stopped.

In general, when an aqueous solution of an ethylene oxide-type nonionic surface active agent is heated to an elevated temperature, the solution becomes turbid at a certain temperature. This temperature is called the "cloud point". In ethylene oxide-type nonionic surface active agents, the cloud point is generally lower as the length of the ethylene oxide chain is shorter, and also, as the surface active agent concentration in the aqueous solution is lower, the cloud point is lower.

The oxidation reaction using a noble metal catalyst must be carried out at a temperature higher than about 60° C. in order to maintain a high reaction rate. However, in most ethylene oxide-type nonionic surface active agents having a short chain length, the cloud point is much lower than that reaction temperature, and even if the concentration in the aqueous solution is elevated to increase the cloud point, no sufficient increase of the cloud point can be attained. Therefore, according to the existing knowledge, it is presumed that most nonionic surface active agents having a short ethylene oxide chain are not suitable for the oxidation reaction according to the above known process because the reaction mixture is separated into aqueous and oil phases under optimum reaction conditions. In contrast, according to the process of the present invention, even if the ethylene oxide chain of the starting nonionic surface active agent is short, and both aqueous and oil phases are present in the reaction mixture, the reaction advances smoothly. The reasons for this unexpectedly different property are not completely elucidated, but it is believed that ethylene oxide-type nonionic surface active agents are different from ordinary alcohols in that they have a surface activity. More specifically, it is considered that while an oil phase is completely separated from an aqueous phase in the case of ordinary alcohols, in the case of an ethylene oxide-type nonionic surface active agent, the primary hydroxy group, the reactive terminal, is oriented to the aqueous phase and a homogeneous solution is locally formed. Incidentally, for ethylene oxide-type nonionic surface active agents, even if the oil phase is separated, there is no risk of explosion, because a considerable amount of water is contained in this oil phase.

The present invention relates to a process in which ether type nonionic surface active agents having a polyoxyethylene chain can be advantageously oxidized regardless of whether the ethylene oxide chain is long or short and regardless of whether they are water-soluble or water-insoluble.

More specifically, in accordance with the present invention, there is provided a process for oxidizing nonionic surface active agents comprising contacting a nonionic surface active agent represented by the following general formula:

RO(EO)$_n$H wherein EO stands for ethylene oxide, R is octylphenyl, nonylphenyl, dodecylphenyl or alkyl having 8 to 22 carbon atoms, and n is an integer from 1 to 100, or a nonionic surface active agent consisting of oxyethyleneoxypropylene block copolymers having an average molecular weight of 1000 to 12000 in which the ratio of the polyoxyethylene chain to the total molecular weight is 10 to 80% by weight, with oxygen, in the presence of a palladium catalyst, at a pH of from 8 to 13 and at a temperature of 50° to 95° C.

Ethylene oxide-type nonionic surface active agents suitable for the oxidation process of the present invention are represented by the general formula RO(EO)$_n$H and they are prepared by adding n molecules of ethylene oxide to ROH. The compound of the formula ROH is a linear primry alcohol, a branched primary alcohol, a secondary alcohol, an alkyl phenol or mixture thereof. These alcohols can include an unsaturated bond in the molecule. Other nonionic surface active agents suitable for the process of the present invention are ethylene oxide-propylene oxide block copolymers.

Pure oxygen is most preferred as the oxidizing gas to be used in the present invention, but any gas having an oxygen concentration of at least 95% can be used. When the reaction temperature is high, the partial pressure of water becomes high with lowering in partial oxygen pressure. Accordingly, in such cases, it is preferred to use pressurized oxygen. In general, good results are obtained when the oxygen pressure is from zero to 3 Kg/cm$^2$ gauge. It is preferred that the reaction be carried out in a closed reaction vessel and that the oxygen be supplied at a rate corresponding to the rate at which oxygen is consumed. When air is used, non-reactive nitrogen should always be expelled from the reaction vessel. In this case, the reaction product is lost in the form of entrained foams, together with nitrogen. Accordingly, the use of air is not preferred. A catalyst comprising metallic palladium supported on an inactive carrier is preferred as the palladium catalyst. A catalyst comprising 1 to 10 wt. % of Pd supported on carbon is especially preferred. An appropriate amount of the catalyst is 0.5 to 10% by weight, based on the weight of the starting ether-type nonionic surface active agent. The reaction temperature is 50° to 90° C., preferably 60° to 85° C. When the reaction temperature is low, the reaction rate is reduced, and when the reaction temperature is too high, the reaction product is colored. In general, the reaction time is 1 to 5 hours.

In carrying out the process of the present invention, the reaction mixture is agitated in order to attain good contact between oxygen and the catalyst. When the agitation is weak, insufficient contact is attained and the reaction rate is lowered. When the agitation is too strong, foaming becomes extreme and contact between oxygen and the catalyst is worsened again and the reaction is stopped in some cases. Accordingly, it is preferred that the agitation be carried out as vigorously as possible, provided that foaming is avoided.

The carboxylic acid formed by the reaction should be neutralized with an alkali. A caustic alkali is preferred as the alkali, and caustic soda is especially preferred. In this case, the pH should be controlled within the range of from 8 to 13. When the pH is too low, the reaction rate is low, and when the pH is too high, the reaction product is extremely colored.

When the reaction is carried out under the above-mentioned conditions, the reaction is ordinarily completed within about 4 hours. The yield is generally 80 to 95%. This is a very high yield and is much higher than the yields obtained using the known techniques. The yield can be determined by rendering the reaction product mixture acidic by adding hydrochloric acid, extracting the mixture with chloroform and calculating the yield from the acid value and hydroxyl value of the extract. The yield can also be determined from the NMR spectrum of the above extract. According to the process of the present invention, significant amounts of impurities are not formed and cleavage of the ether linkage does not occur.

The present invention will now be further described in detail by reference to the following illustrative Examples.

EXAMPLE 1

In a 1-liter autoclave equipped with a rotary agitator, there were charged 100 g of polyoxyethylene lauryl ether (the average number of added moles of ethylene oxide being 4.2) and 500 g of water containing 5 g of a 5%-Pd/carbon catalyst. Air in the reaction vessel was replaced with oxygen and the temperature of the mixture was elevated to 70° C. under agitation. The oxygen pressure in the reaction vessel was adjusted to 1.5 Kg/cm$^2$ (gauge). A 20% caustic soda aqueous solution was continuously added to maintain the pH of the reaction mixture at 10 to 13, while oxygen was supplied so that the oxygen pressure was maintained at 1.5 Kg/cm$^2$ (gauge). Two hours after the beginning of the addition of caustic soda, the absorption of oxygen became very slow and the reaction was completed. The amount of the 20% caustic soda solution added during the reaction was 51 g, which corresponds to 94% of the calculated value. The catalyst was removed from the reaction mixture by filtration and there was obtained an aqueous solution of $C_{12}H_{25}O(CH_2CH_2O)_n$–$CH_2COONa$ ($\bar{n}=3.2$), having a hue of APHA 40. The aqueous solution was rendered acidic by adding hydrochloric acid and then was extracted with chloroform. From the results of IR (infrared spectroscopy), NMR (nuclear magnetic resonance spectroscopy) and chemical analyses of the extract, it was found that the intended product was formed. Since the extract had an acid value of 132 and a hydroxyl value of 13.6, it was found that the conversion was 91%.

EXAMPLES 2 TO 7

The nonionic surface active agents shown in Table I were oxidized using the same reaction vessel as used in Example 1, under the same reaction conditions as described in Example 1, except that the reaction temperature was changed as indicated in Table I. The results obtained are shown in Table I.

Each of the starting nonionic surface active agents used had a cloud point lower than 50° C. or was not completely dissolved in water.

In Table I, POE represents polyoxyethylene and $\bar{p}$ represents an average number of added moles of ethylene oxide.

Table I

| Ex. No. | Nonionic Surface Active Agent | $\bar{p}$ | Reaction Temperature (°C.) | Conversion (%) |
|---|---|---|---|---|
| 2 | POE nonyl phenyl ether | 5 | 75 | 82 |
| 3 | POE sec-alkyl ether | 5 | 70 | 94 |
| 4 | POE oleyl ether | 3 | 68 | 88 |
| 5 | POE lauryl ether | 4 | 80 | 90 |

Table I-continued

| Ex. No. | Nonionic Surface Active Agent | $\bar{p}$ | Reaction Temperature (°C.) | Conversion (%) |
|---|---|---|---|---|
| 6 | POE oxoalcohol ether | 4.5 | 70 | 90 |
| 7 | oxyethylene-oxypropylene block copolymer | molecular weight = 2500 | 70 | 81 |

Note

The alkyl group of the surface active agent of Example 3 had 13 carbon atoms, the alkyl group of the surface active agent of Example 6 had 12.5 carbon atoms on the average, and in the copolymer of Example 7, the content of the polyoxyethylene chain is 28 wt. %.

EXAMPLE 8

A reaction was carried out using the same reaction vessel and under the same reaction conditions as described in Example 1, except that the catalyst recovered in Example 1 was used.

The reaction was stopped at 90 minutes after the start of the reaction, when the oxygen absorption was very slow. An aqueous solution of the reaction product having a hue of APHA 50 was obtained. The conversion was 90%.

EXAMPLE 9

In a 1-liter autoclave equipped with a rotary agitator, there were charged 150 g of polyoxyethylene sec-alkyl ether (the same as used in Example 3) and a suspension of 6 g of a 5%-Pd/carbon catalyst in 500 g of water, and air in the reaction vessel was replaced with oxygen. The temperature was elevated to 75° C. and the oxygen pressure was maintained at 2.5 Kg/cm$^2$ (gauge). A 1.0% aqueous solution of caustic soda was added to maintain the pH of the reaction mixture at 9 to 12, and the oxygen pressure was maintained at 2.5 Kg/cm$^2$ (gauge). After 2.5 hours had passed from the start of the reaction, the oxygen absorption became very slow and the reaction was completed. The catalyst was removed by filtration. There was obtained an aqueous solution of the product having a hue of APHA 120. The conversion was 86%.

EXAMPLE 10

In a 1-liter autoclave equipped with a rotary agitator, there were charged 150 g of polyoxyethylene lauryl ether (the average number of added moles of ethylene oxide being 11.1) and a suspension of 6 g of a 5%-Pd/carbon catalyst in 500 g of water, and air in the reaction vessel was replaced with oxygen. The temperature of the reaction mixture was elevated to 75° C. under agitation. A 20% caustic soda solution was added to maintain the pH at 9 to 13, and oxygen was supplied to maintain the pressure at 2.0 Kg/cm$^2$ (gauge). After 90 minutes from the beginning of the addition of caustic soda, the reaction was stopped and the catalyst was removed from the reaction mixture by filtration. The APHA of the filtrate was 40. From the results of IR, NMR and chemical analyses of the chloroform extract of the reaction mixture which had been rendered acidic by hydrochloric acid, it was confirmed that the product was an aqueous solution of $C_{12}H_{25}O(CH_2CH_2O)_n$CH$_2$COONa ($\bar{n}=10.1$), and the chloroform extract was found to have an acid value of 75.9 and a hydroxyl value of 5.5, from which it was confirmed that the conversion to the intended product was 93%.

EXAMPLE 11

In a 1-liter autoclave equipped with a rotary agitator, there were charged 200 g of polyoxyethylene (the number of added moles of ethylene oxide being 9) sec-alkyl ether (having 13 carbon atoms) and a suspension of 8 g of 5%-Pd/carbon catalyst in 400 g of water. Air in the reaction vessel was replaced with oxygen and the temperature of the reaction mixture was elevated to 60° C. A 25% aqueous solution of caustic soda was added to maintain the pH of the reaction mixture at 9 to 12 and the oxygen pressure was maintained at 0 to 2.5 Kg/cm$^2$ (gauge). When 3 hours had passed from the start of the addition of the aqueous solution of caustic soda, the catalyst was removed from the reaction mixture by filtration. The APHA of the filtrate was 30, and from the results of IR, NMR and chemical analyses of the chloroform extract of the reaction product which had been rendered acidic by hydrochloric acid, it was confirmed that the intended product was formed. From the facts that the chloroform extract had an acid value of 87.9 and a hydroxyl value of 9.5, it was found that the conversion to the extended product was 90%.

EXAMPLES 12 TO 17

Oxidations of nonionic surface active agents indicated in Table II were carried out in the same reaction vessel under the same reaction conditions as described in Example 11. The results shown in Table II were obtained.

In Table II, POE stands for polyoxyethylene and $\bar{p}$ stands for the average added mole number.

Table II

| Ex. No. | Nonionic Surface Active Agent | $\bar{p}$ | Cloud Point (°C.) | Conversion (%) |
|---|---|---|---|---|
| 12 | POE lauryl ether | 9 | 78 | 92 |
| 13 | POE stearyl ether | 11 | 100< | 95 |
| 14 | POE nonyl phenyl ether | 9 | 74 | 87 |
| 15 | POE oleyl ether | 8 | 90 | 82 |
| 16 | POE oxoalcohol ether | 8 | 62 | 90 |
| 17 | oxyethylene-oxypropylene block copolymer | molecular weight = 2,000 | 60 | 81 |

Note

The alkyl group of the nonionic surface active agent of Example 16 has 12 carbon atoms, and the polyoxyethylene chain content in the copolymer of Example 17 is 46%.

The embodiments of the invention in which an exclusive property or privilege is claimed are defined as follows:

1. A process for preparing an ether carboxylate, which comprises the steps of: intimately contacting, at a temperature of 50° to 95° C., oxygen gas with a liquid reaction mixture consisting essentially of a material selected from the group consisting of (a) a compound or mixture of compounds having the formula RO(CH$_2$CH$_2$O)$_n$H wherein R is octylphenyl, nonylphenyl, dodecylphenyl or alkyl having 8 to 22 carbon atoms, and n is an integer of from 1 to 100, (b) oxyethylene-oxypropylene block copolymer having an average molecular weight of from 1000 to 12000 and containing from 10 to 80% by weight of ethylene oxide units, and mixtures thereof, dissolved or dispersed in water, said reaction mixture containing from 0.5 to 10% by weight of catalyst based on the weight of said material, said catalyst being composed of an inactive carrier having from 1 to 10% by weight of palladium supported on said carrier, said reaction mixture also containing caustic alkali so that said reaction mixture has a pH of from 8 to 13, the oxygen gas being contacted with said reaction mixture for a period of time effective to transform said material to the corresponding carboxylate.

2. A process according to claim 1 wherein said carrier is carbon.

3. A process according to claim 1 in which said material is component (a) wherein R is alkyl having 8 to 22 carbon atoms.

4. A process according to claim 1 in which said material is component (a) wherein R is octylphenyl, nonylphenyl or dodecylphenyl.

5. A process according to claim 1 in which said material is component (b).

6. A process according to claim 1 wherein the caustic alkali is caustic soda.

7. A process according to claim 1 wherein said material is dissolved or dispersed in water at a concentration of 10 to 40% by weight.

8. A process for preparing an ether carboxylate, which comprises the steps of mixing in a closed reaction vessel, water, a palladium-on-carbon catalyst containing from 1 to 10% by weight of palladium and a material selected from the group consisting of (a) a compound or mixture of compounds having the formula RO(CH$_2$CH$_2$O)$_n$H wherein R is octylphenyl, nonylphenyl, dodecylphenyl or alkyl having 8 to 22 carbon atoms, and n is an integer of from 1 to 100, (b) oxyethylene-oxypropylene block copolymer having the formula HO(CH$_2$CH$_2$O)$_a$(C$_3$H$_6$O)$_b$(CH$_2$CH$_2$O)$_c$H, wherein the values of a, b and c are such that said copolymer has an average molecular weight of from 1000 to 12000 and contains from 10 to 80% by weight of ethylene oxide units, and mixtures thereof, to form a liquid reaction mixture containing 10 to 40% by weight of said material and containing from 0.5 to 10% by weight of said catalyst based on the weight of said material, replacing the atmosphere in said vessel with oxygen and maintaining the oxygen pressure in said vessel in the range of 0 to 3 Kg/cm$^2$ gauge, maintaining the temperature of the reaction mixture at from 50° to 95° C., adding caustic alkali to the reaction mixture to maintain the pH thereof at from 8 to 13 and agitating the reaction mixture to effect intimate contact of oxygen with the reaction mixture, without causing foaming of the reaction mixture, for a period of from about 1 hour to about 5 hours whereby to transform said material to the corresponding carboxylate.

* * * * *